US00PP21397P3

(12) United States Plant Patent
Bourne

(10) Patent No.: US PP21,397 P3
(45) Date of Patent: Oct. 19, 2010

(54) ***DIANTHUS* PLANT NAMED 'WP08 ROS03'**

(50) Latin Name: *Dianthus×hybrida*
Varietal Denomination: WP08 ROS03

(76) Inventor: Carolyn Grace Bourne, Houndspool, Ashcombe Road, Dawlish, Devon (GB) EX7 0QP ( * ) Notice: Subject to any disclaimer, the term of this patent is extended or adjusted under 35 U.S.C. 154(b) by 0 days.

(21) Appl. No.: 12/456,954

(22) Filed: Jun. 24, 2009

(65) Prior Publication Data

US 2009/0328264 P1 Dec. 31, 2009

(51) Int. Cl.
*A01H 5/00* (2006.01)

(52) U.S. Cl. ..... Plt./281

(58) Field of Classification Search ..... Plt./281
See application file for complete search history.

*Primary Examiner*—Annette H Para

(57) ABSTRACT

A new cultivar of *Dianthus* plant named 'WP08 ROS03' that is characterized by upright, vase-shaped habit, semi-double flowers which are uniformly deep salmon-pink in color and which bloom profusely from April until October. In combination these traits set 'WP08 ROS03' apart from all other existing varieties of *Dianthus* known to the inventor.

2 Drawing Sheets

Genus: Dianthus.
Species: ×*hybrida*.
Denomination: 'WP08 ROS03'.

BACKGROUND OF THE INVENTION

This application claims the benefit of priority under 35 U.S.C. 119(f) of the application for a grant of European Community Plant Breeders Rights which was filed for the instant plant variety on Jun. 30, 2008, Application Number 2008/1509.

The present invention relates to a new and distinct cultivar of hardy garden pink or carnation which is grown for use as a flowering plant for pots and containers and for planting in the garden or landscape. The new cultivar is known botanically as *Dianthus×hybrida* and will be referred to hereinafter by the cultivar name 'WP08 ROS03'.

'WP08 ROS03' is a complex hybrid plant that is the product of a breeding program started by the inventor in 1985 and conducted in a cultivated area of Houndspool, Dawlish, Devon, United Kingdom. The inventor selected 'WP08 ROS03' in 2004 for its flowers that are deep salmon pink in color and semi-double in form.

'WP08 ROS03' resulted from the controlled pollination between two unreleased and unpatented varieties, namely *Dianthus* code number ASH20 as female parent plant and *Dianthus* code number 99.17 as male parent plant.

'WP08 ROS03' is distinguishable from the female parent as follows: The female parent has semi-double carmine flowers. The female parent is less vigorous than 'WP08 ROS03'. The flowers of the female parent are also smaller and are pink with a darker pink eye.

'WP08 ROS03' is distinguishable from the male parent as follows: The male parent is much taller in height and has large single flowers which are colored carmine with a white border. In addition, the foliage of 'WP08 ROS03' is green whereas the color of the foliage of the male parent is gray-green.

The variety of *Dianthus* which is considered by the inventor to most closely resemble 'WP08 ROS03' is the inventor's variety *Dianthus* 'Stardust' (U.S. Plant patent application Ser. No. 12/228,983, filed on Aug. 8, 2008). 'Stardust' bears flowers which are double in form and pale pink in color.

Asexual reproduction of the new cultivar 'WP08 ROS03' was first accomplished by the inventor in 2004 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'WP08 ROS03'. These traits in combination distinguish this cultivar from all other commercial varieties known to the inventor. 'WP08 ROS03' has not been tested under all possible conditions and phenotypic differences may be observed with variations in environmental, climatic and cultural conditions, however, without any variance in genotype.

1. *Dianthus* 'WP08 ROS03' exhibits an upright, vase-shaped plant habit.
2. *Dianthus* 'WP08 ROS03' blooms profusely from April until October.
3. *Dianthus* 'WP08 ROS03' bears semi-double flowers which are uniformly deep salmon-pink in color.
4. *Dianthus* 'WP08 ROS03' exhibits green foliage.
5. At maturity, the height of the foliage mound of *Dianthus* 'WP08 ROS03' is 15 cm to 20 cm; the width is 10 cm to 12 cm.
6. *Dianthus* 'WP08 ROS03' is perennial and is hardy to −15° C.

BRIEF DESCRIPTION OF THE DRAWINGS

The accompanying color drawings illustrate the overall appearance of the new *Dianthus* variety 'WP08 ROS03' showing colors as true as it is reasonably possible to obtain in colored reproductions of this type. Colors in the drawings may differ from the color values cited in the detailed botanical description, which accurately describe the actual colors of the new variety 'WP08 ROS03'.

The drawing labeled as FIG. 1 depicts an entire flowering plant.

Figure 1:
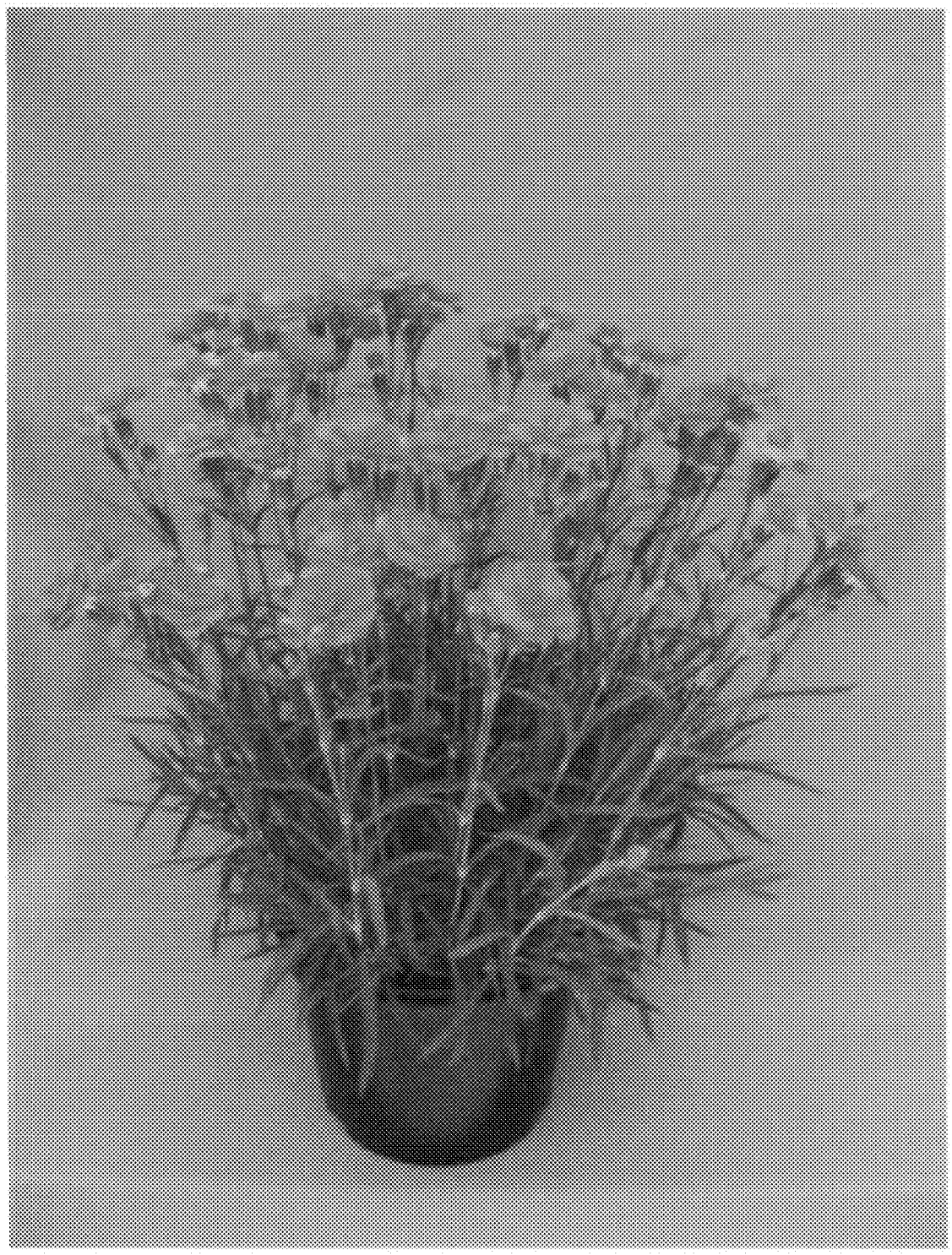
Figure 2:
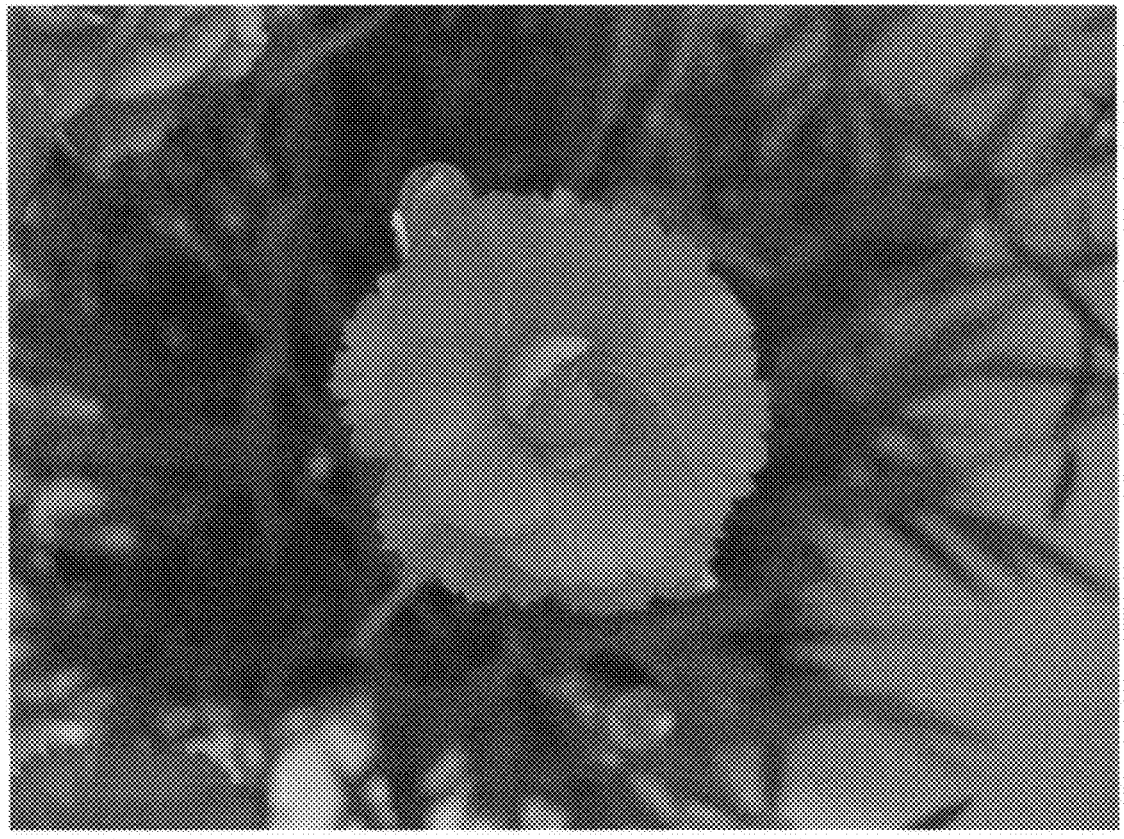

The drawing labeled as FIG. 2 depicts a close-up view of the flower.

All drawings were made of 9 months old plants which have been grown in 1.5-liter containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP08 ROS03'. Data was collected in spring from 1.5-liter container plants in spring, and grown indoors in Devon, United Kingdom. The color determinations are in accordance with the 2007 edition of The Royal Horticultural Society Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical classification:
- *Family.*—Caryophyllaceae.
- *Genus.*—Dianthus.
- *Species.*—×*allwoodii*.
- *Denomination.*—'WP08 ROS03'.

Parentage: A complex *Dianthus* hybrid whose immediate parents are unreleased hybrids from the inventor's breeding program, identified as follows:
- *Male parent.*—Selection 99.17.
- *Female parent.*—Selection ASH20.

Use of plant: As a flowering plant in containers, window boxes, planters, pots and the garden.

Bloom period: April-October.

Plant habit: Upright vase-shaped with dense branching.

Height of plant: 15 to 20 cm after 9 months.

Width of plant: 10 to 12 cm after 9 months.

Hardiness: Hardy at least to minus 15 Centigrade.

Plant type: Perennial herb.

Root system: many fibrous roots.

Propagation method: by vegetative stem cuttings.

Cultural requirements: Grow in full sun, in well drained and moderately fertile soil, keep well fertilized and watered.

Diseases and pests: No particular resistance or susceptibility to *Dianthus* diseases and pests are known to the inventor.

Time to root cuttings: 5 weeks is required to produce roots on a vegetative cutting.

Temperature for rooting: A minimum of 15° C. air temperature and 21° C. base temperature at root level is required to produce roots on the cuttings.

Facilities for rooting: A mist propagation unit is required for satisfactory rooting of cuttings.

Crop time: 3 months starting in the Spring and 6 months starting in the Fall.

Plant stem:
- *Shape.*—Cylindrical.
- *Dimensions.*—
- *Height.*—7 to 9 cm.
- *Diameter.*—3 to 4 mm.
- *Surface.*—Glabrous and glaucous.
- *Color.*—145B, 145C at the node.
- *Branching.*—Numerous shoots from the axils of the lower leaves.
- *Internode length* (*between nodes*).—8 to 10 mm.

Leaf:
- *Type.*—Evergreen.
- *Shape.*—Linear, straight.
- *Division.*—Simple.
- *Apex.*—Acute.
- *Base.*—Decurrent.
- *Venation.*—Not prominent.
- *Margins.*—Entire.
- *Arrangement.*—Opposite and spiraling on stem.
- *Attachment.*—Sheathing.
- *Surface adaxial.*—Glaucous.
- *Surface abaxial.*—Glaucous.
- *Fragrance.*—Absent.
- *Dimensions.*—Length: 50 to 60 mm. Width: 4 mm.
- *Color.*—Adaxial surface: N138A. Abaxial surface: N138A.

Inflorescence:
- *Flower stem dimension.*—Length: 10 to 15 cm. Width: 2 mm. Stem strength: Erect. Color: 133B to 133C.
- *Type.*—Cymose.
- *Form.*—Salviform, symmetrical.
- *Development.*—Singly, in sequence from the uppermost bud.

Bud:
- *Color.*—183D.
- *Dimensions.*—15 mm in length and 99 mm in width.
- *Shape.*—Cylindrical.

Flowers:
- *Number.*—3 to 5 per stem.
- *Dimensions.*—Length including calyx: 31 to 33 mm. Diameter: 30 to 32 mm.
- *Flower shape.*—Circular.
- *Flower profile.*—Flat to convex.
- *Lastingness.*—10 days at 20° C., on or off the plant.
- *Fragrance.*—Delicate.
- *Flowering period.*—April to October.

Corolla:
- *Shape* (*upper part of corolla*).—Convex.
- *Shape* (*lower part of corolla*).—Flat.
- *Petal arrangement.*—Persistent, semi-double, overlapping.
- *Petal margin.*—Crenate-dentate.
- *Indentation.*—0.5 to 1 mm deep.
- *Petal texture.*—Soft.
- *Flower type.*—Semi-double.
- *Petal number.*—10 to 15.
- *Petal dimension.*—Length: 32 to 34 mm. Width: 17 mm.
- *Color pattern.*—Uniform, self-colored throughout.
- *Color of upper surface.*—Ground color of blade: 52B. Color of middle of strap (basal attachment): 145C. Color of base of strap: 145D.
- *Color of lower surface.*—Ground color of blade: 52B to 52C. Color of middle of strap: 145C. Color of base of strap: 145D.
- *Petal shape.*—Obdeltoid.
- *Petal surface.*—Glabrous, flat.

Calyx:
- *Shape.*—Cylindrical.
- *Longitudinal profile.*—Flat.
- *Dimensions.*—Length: 19 to 20 mm. Diameter: 7 mm.

*Sepals.*—Fused.
*Sepals number.*—5.
*Sepals color.*—143A at apex, 145B elsewhere.
*Anthocyanin.*—No.
*Splitting.*—No.

Epicalyx:
*Bracts number.*—1 pair of 2.
*Shape of outer lobe.*—Acuminate.
*Dimensions.*—Width: 5 mm. Length: 6 mm.
*Color.*—N138A at the apex; 142C elsewhere.
*Anthocyanin.*—Absent.

Bracteoles:
*Number.*—1 pair of 2.
*Dimensions.*—Width: 7 to 8 mm. Length: 6 to 8 mm.
*Color.*—N138A on the tip and 142C on sides.
*Anthocyanin.*—Absent.

Reproductive organs:
*Stamens.*—Number: 2. Color of filaments: White. Dimensions: Length: 18 to 22 mm. Diameter: 0.5 mm.
*Anthers.*—Number: 5 with usually 5 additional petaloid anthers. Color: 73B to 73C. Dimensions: Length: 2 to 3 mm. Diameter: 1 mm. Attachment: Dorsifixed. Pollen: Present occasionally. Color: 157A.
*Style.*—Number: 2. Shoulder: Absent. Color: White.
*Dimensions* (*at maturity style and stigma*).—Length: 25 mm. Width: 0.5 to 1 mm.
*Stigma.*—Number: One per style. Color: 59D. Dimensions: 5 to 8 mm above flower.
*Ovary.*—Position: Superior. Dimensions: Length: 8 mm. Diameter: 5 mm. Shape: Spindle. Color upper: 145A to 143C. Color lower: 145C.
*Seed.*—Not observed.

The invention claimed is:

1. A new and distinct cultivar of *Dianthus* plant named 'WP08 ROS03' as described and illustrated herein.

* * * * *